United States Patent [19]

Lukacsek

[11] 4,271,270
[45] Jun. 2, 1981

[54] APPARATUS FOR CULTURING AND EXAMINING FUNGI

[76] Inventor: Patricia A. Lukacsek, 4014 W. Navaj Dr., Phoenix, Ariz. 85021

[21] Appl. No.: 63,952

[22] Filed: Aug. 6, 1979

Related U.S. Application Data

[60] Division of Ser. No. 845,897, Oct. 27, 1977, which is a continuation-in-part of Ser. No. 789,773, Apr. 22, 1977, abandoned.

[51] Int. Cl.³ .............................................. C12M 1/28
[52] U.S. Cl. ................................. 435/294; 435/297; 435/298; 435/299
[58] Field of Search .............. 435/294, 297, 298, 299, 435/301

[56] References Cited

U.S. PATENT DOCUMENTS

| 3,563,859 | 2/1971 | Fink | 435/294 |
| 3,684,660 | 8/1972 | Kereluk et al. | 435/298 |
| 3,817,839 | 6/1974 | Warren | 435/294 |
| 3,928,136 | 12/1975 | Launey | 435/299 |

OTHER PUBLICATIONS

Bronfenbrenner, American Journal of Public Health vol. 8, pp. 922 and 923 (1918).

Primary Examiner—Alvin E. Tanenholtz
Attorney, Agent, or Firm—Herbert E. Haynes, Jr.

[57] ABSTRACT

An apparatus for culturing and examination of fungi is configured to maintain the sterility of a culture medium and a cover slip until ready for use in accordance with a method which cultures the fungi in an environment which remains undisturbed during microscopic examination of the cultured fungi.

6 Claims, 4 Drawing Figures

U.S. Patent  Jun. 2, 1981  4,271,270
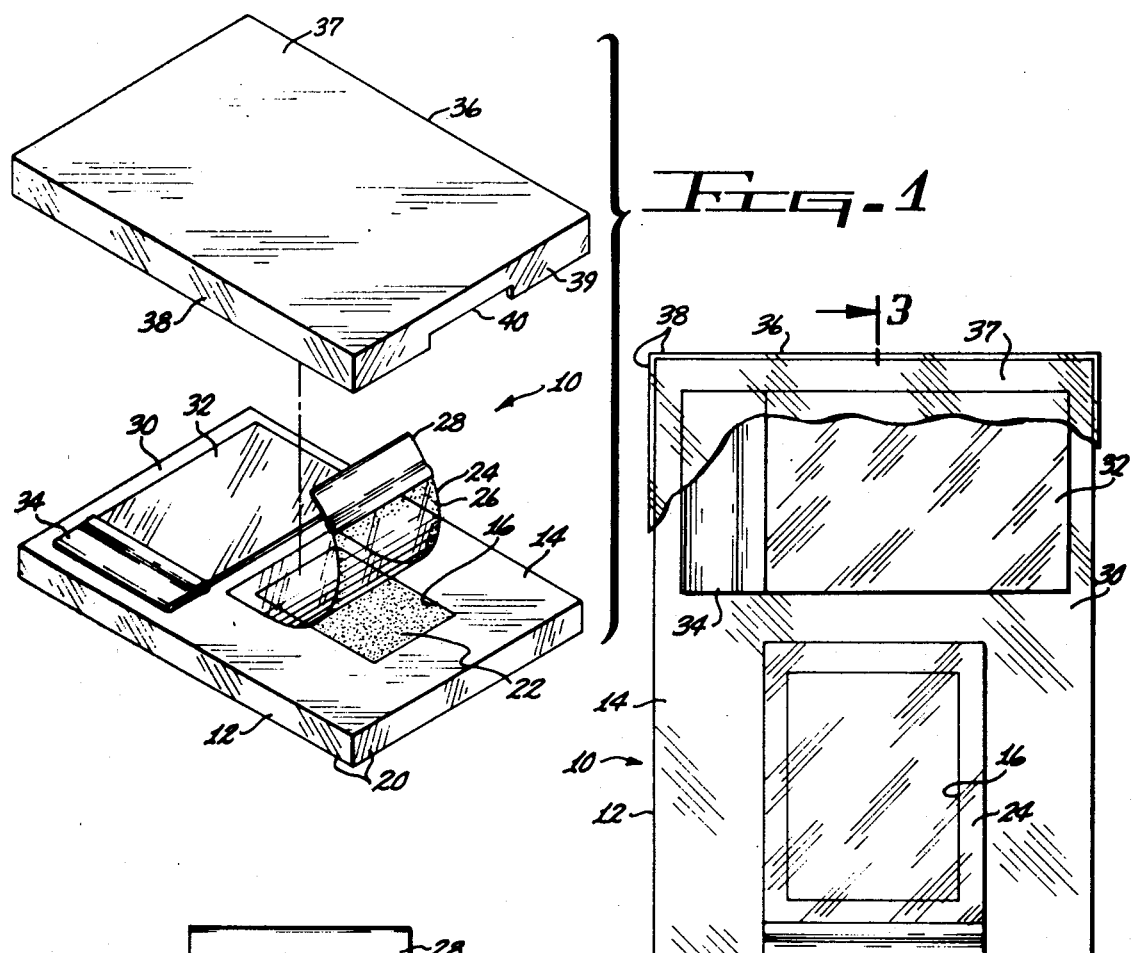
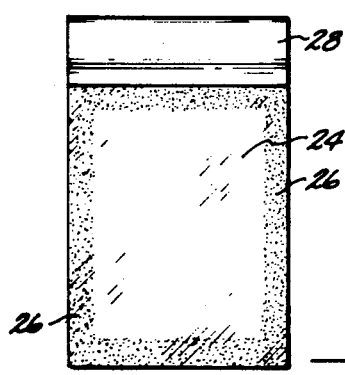
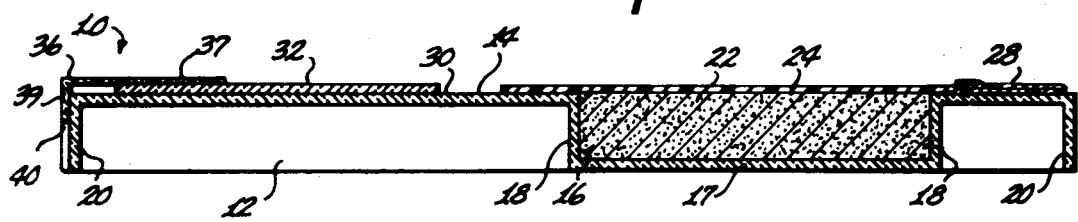

APPARATUS FOR CULTURING AND EXAMINING FUNGI

CROSS-REFERENCE TO RELATED APPLICATION

This application is a Divisional of Copending U.S. Patent Application Ser. No. 845,897, filed Oct. 27, 1977 for: METHOD AND APPARATUS FOR CULTURING AND EXAMINING FUNGI. The prior Pending Application is in turn a continuation-in-part of copending U.S. Patent Application Ser. No. 789,773, filed Apr. 22, 1977 by the same inventor and which is now abandoned.

BACKGROUND OF THE INVENTION

1. Field of the Invention

This invention relates to microbiology, and more particularly to a method and apparatus for the culturing and examination of fungi.

2. Description of the Prior Art

As is well known in the art, the culturing and examination of fungi is a procedure which must be accomplished with sterilized equipment and under controlled conditions to prevent contamination of the cultured fungi as such contamination can produce unsuccessful and/or misleading results, and to prevent the cultured fungi from in turn, contaminating laboratory equipment and personnel.

The most commonly used prior art method and apparatus comprises a round petrie dish which is filled with water to a depth which partially submerges a spaced pair of horizontally disposed supports such as toothpicks. A standard microscope slide is placed atop the toothpicks and a suitable culture nutrient medium such as agar is applied to the upper surface of the slide. The culture medium is then inoculated with the fungi and a standard cover slip is placed atop the inoculated medium. The petrie dish is then covered with a standard petrie dish lid, and after a suitable incubation period, the petrie dish lid is removed and the cover slip, cultured fungi, agar, and microscope slide are then lifted as a unit from the petrie dish and placed upon the stage of a microscope for examination purposes. If desired, a permanent record of the cultured fungi may be made by the well known staining method.

The above described prior art apparatus and method has several drawbacks and shortcomings. In the first place, the relatively complex setup procedure and equipment handling is not conducive to the prevention of contamination of the cultured fungi. Secondly, the precarious positioning of the microscope slide, inoculated cultured medium, and cover slip on the toothpicks requires that extreme care be exercised to prevent jarring or otherwise upsetting the apparatus during the incubation period as the water in the petrie dish must not be allowed to contact the inoculated culture medium. Further, the lifting as a unit, of the slide, medium, cultured fungi, and cover slip for placement on the stage of a microscope can easily result in the cultured fungi contaminating the lab equipment and personnel.

In addition to the above described shortcomings, the prior art method and apparatus has other drawbacks in that excessive lab time must be expended in sterilization and setting up of the equipment, handling of the round petrie dish is awkward, the quantity of the culture medium is inconsistent, and the equipment must be monitored to insure that the water in the petrie dish is not allowed to evaporate.

Therefore, a need exists for a new and improved method and apparatus for culturing and examining fungi which overcomes some of the drawbacks and shortcomings of the prior art.

SUMMARY OF THE INVENTION

In accordance with the present invention, a new and improved method and apparatus is disclosed for culturing and examining fungi.

The apparatus of the present invention includes a base formed of optically clear material and which is configured to provide a compartment which opens upwardly onto a planar top surface. The compartment is filled with a suitable jelled culture nutrient medium, such as agar, so that the medium is flush with the planar top surface of the base. A membrane is removably affixed to the planar top surface so as to sealingly enclose the culture medium to prevent contamination thereof and to prevent evaporation of the moisture in the culture medium. A sterilized cover slip is supported on the planar surface of the base, and a base cover of optically clear material is employed for enclosing the base to maintain sterility.

The apparatus of the present invention as described above may be prepared either in a laboratory or at some other suitable location and may be stored for an indefinite period of time until ready for use.

The apparatus as described above is used for culturing and examining fungi in accordance with the method of the present invention which includes the following steps. The base cover is removed to expose the top planar surface of the base and the sealing membrane is removed to expose the culture medium. A suitable fungi is inoculated into the culture medium and cover slip is placed upon the inoculated medium so as to be in contiguous engagement therewith. The cover slip is larger than the opening of the compartment, therefore, the peripheral edges of the cover slip rests on the planar surface immediately surrounding the compartment and thus sealingly encloses the compartment. The base cover is then replaced and remains in that position during and after the incubation period so that the apparatus in its entirety is placed upon the stage of a microscope for examination of the cultured fungi therein. Since the base and base cover are formed of optically clear material, the examination of the cultured fungi may be accomplished without disturbing the environment in which it was cultured.

It will now be seen that the method and apparatus of the present invention has substantially reduced the possibility of contamination of the cultured fungi and contamination of lab equipment and personnel by the cultured fungi. Other drawbacks of the prior art are eliminated, or at least, substantially reduced, in that set up time is reduced, no water other than the moisture in the culture medium is needed, and handling of the cultured fungi is eliminated. With the base cover in place, no special handling, monitoring, or other care must be exercised during the incubation period.

Accordingly, it is an object of the present invention to provide a new and improved apparatus for culturing and examining fungi.

Another object of the present invention is to provide a new and improved apparatus for culturing and examining fungi, with the apparatus adapted for sterilization and preparation at any suitable location and capable of being stored until ready for use.

Another object of the present invention is to provide a new and improved apparatus for culturing and examining fungi, with the apparatus being adapted for containing a culture nutrient medium in a sealed environment to prevent contamination and/or dehydration thereof until ready for use.

Another object of the present invention is to provide an apparatus of the above described character which includes a base configured with a compartment opening upwardly onto a planar top surface with the culture medium in the compartment and flush with the planar surface, and a removable membrane sealingly enclosing the culture medium within the compartment.

Another object of the present invention is to provide an apparatus of the above described character in which a sterilized cover slip is supported on the planar surface of the base adjacent the compartment thereof, and a base cover encloses the base to maintain the sterility of the apparatus until ready for use.

Another object of the present invention is to provide an apparatus of the above described character in which the base and base cover are formed of optically clear material to allow microscopic examination of the culture medium after inoculation and incubation of a fungi therein, without the necessity of removing it from the apparatus.

Another object of the present invention is to provide a new and improved method for culturing and examining fungi.

Another object of the present invention is to provide a new and improved method for culturing and examining fungi which minimizes the possibility of contamination of the cultured fungi.

Another object of the present invention is to provide a new and improved method for culturing and examining fungi which substantially reduces the possibility of the cultured fungi contaminating the lab equipment and/or personnel.

Another object of the present invention is to provide a new and improved method for culturing and examining fungi in which the culturing is accomplished within an optically clear apparatus so that microscopic examination of the cultured fungi may be accomplished without removing the cultured fungi therefrom.

Another object of the present invention is to provide a new and improved method for culturing and examining fungi which includes the steps of: placing a culture nutrient medium in a compartment which opens upwardly onto a planar surface of an optically clear base with the culture medium being flush with the planar surface thereof, inoculating the culture medium with a fungi, placing a cover slip over the compartment for sealed enclosing thereof with the cover slip in contiguous engagement with the inoculated culture medium, enclosing the base and cover slip with an optically clear base cover, incubating the fungi and placing the base, base cover, cultured fungi and cover slip as a unit on the stage of a microscope for examination purposes.

The foregoing and other objects of the present invention, as well as the invention itself, may be more fully understood from the following description when read in conjunction with the accompanying drawings.

BRIEF DESCRIPTION OF THE DRAWINGS

FIG. 1 is an exploded isometric view of the apparatus of the present invention illustrating the various features thereof.

FIG. 2 is an enlarged plan view of the apparatus of the present invention and is partially broken away to illustrate the various features.

FIG. 3 is an enlarged sectional view taken along the line 3—3 of FIG. 2.

FIG. 4 is a bottom view of the membrane employed in the apparatus of the present invention.

DESCRIPTION OF THE PREFERRED EMBODIMENT

Referring more particularly to the drawings, FIG. 1 shows the apparatus of the present invention which is indicated in its entirety by the reference numeral 10.

The apparatus 10 includes a base 12 of substantially rectangular planar configuration and having a planar top surface 14. The base 12 is provided with a compartment 16 (FIG. 3) formed therein so as to open upwardly onto the top surface 14. The compartment 16 is defined by a bottom 17 having an endless upstanding side wall 18, with the side wall 18 being integral with the bottom 17 and with the planar top surface 14.

As will become apparent as this description progresses, the base 12 is preferably formed of optically clear material such as glass or any of the well known plastics. In addition to the requirement that the material of which the base is fabricated be optically clear, this material should be relatively rigid and non-porous, and the junctions or corners formed where the bottom 17 and side wall 18 intersect should be square so that light rays may pass through the compartment 16 with minimum refraction thereof.

The preferred configuration of the base 12, as seen best in FIG. 3, is to form the base with the top planar surface 14, with an integral endless side wall 20 depending vertically from the peripheral edges of the surface 14, and with the bottom 17 and endless side wall 18, which define the compartment 16, depending from the planar top surface into the area immediately below that top surface.

The compartment 16 contains a suitable culture nutrient medium 22, such as jelled agar, with the medium 22 filling the compartment 16 so as to be flush with the planar top surface 14 of the base 12.

A protective membrane 24 is removably affixed to the top surface 14 of the base 12 and is disposed thereon so as to sealingly close the top of the compartment 16, and thus prevent contamination of the medium 22, and also prevent dehydration thereof. The membrane 24 may be formed of any suitable transparent nonporous material such as any of the well known plastic materials in sheet or film form. As seen best in FIG. 4, the membrane 24 is provided with a suitable adhesive 26 on the surface thereof which faces the planar top surface 14 of the base 12 when the membrane is positioned thereon. It will be noted that the adhesive 26 is shown as being applied only to the peripheral edges of the membrane 24 which engages the planar top surface 14 when the membrane is positioned as shown in FIG. 2. However, such selective placement of the adhesive is not mandatory in that the undersurface of the membrane could be completely coated with the adhesive 26.

The membrane 24 may be provided with a lift tab 28 suitably affixed to one end thereof to facilitate removal of the membrane to prepare the apparatus 10 for use. The lift tab 28 may be formed of suitable material such as paper which is affixed to the membrane 24 such as with an adhesive (not shown). An alternative to the lift tab 28 may be to form the membrane itself with an extending end (not shown) which is free of any of the adhesive 26.

As shown, the top planar surface 14 of the base 12 is provided with a relatively large area 30 adjacent the compartment 16 thereof, with that area 30 serving as a supporting surface for a standard sterilized cover slip 32. The cover slip 32 is selected from among standard sizes of such structures so that it has a surface area which is larger than the top opening of the compartment 16 of the base 12. The cover slip 32 may be provided with a lift tab 34 affixed to one of the side edges thereof to facilitate handling of the cover slip 32 as will hereinafter be described in detail. Similar to the previously described lift tab 28 of the membrane 24, the lift tab 34 may be formed of any suitable material such as paper and may be affixed to the cover slip 32 with a suitable adhesive.

As seen best in FIG. 1, the apparatus 10 further includes a base cover 36 which is also formed of optically clear material and is configured with a flat planar surface 37 from the peripheral edges of which an endless side wall 38 vertically depends. The base cover 36 is sized so that when placed on the base 12, it will snugly fit over the base with the endless side wall 38 of the cover 36 in contiguous engagement with the outwardly disposed surfaces of the endless side wall 20 of the base 12, as shown in FIG. 2. Each of the opposite end segments 39 (one shown) of the endless side wall 38 of the base cover 36 may be formed with a suitable cutout 40 therein to facilitate removal of the cover 36 from the base 12.

It is to be understood that the apparatus 10 as described above is to be free of any bacteria or other contaminants, and if such is the case and the apparatus 10 is prepared and assembled as hereinbefore described, it can be stored for an indefinite period of time.

When ready for use, the base cover 36 is removed, the membrane 24 is also removed, and the fungi to be cultured and examined is inoculated into the culture medium 22. The sterile cover slip 32 is then placed over the compartment 16 so that the peripheral edges of the cover slip 32 rests on the areas of the top surface 16 which surround the top opening of the compartment 16 and the cover slip 32 is in contiguous engagement with the inoculated culture medium 22. The base cover 36 is then replaced and will hold the cover slip 32 in place atop the inoculated culture medium 22. In this manner, the cover slip 32 will sealingly enclose the inoculated culture medium 22 to prevent contamination and/or dehydration thereof during the incubation period.

When the incubation period is over, the entire apparatus 10 containing the cultured fungi is placed on the stage of a suitable microscope (not shown) for microscopic examination of the cultured fungi. It will be noted that this examination process is made possible due to the fact that the base 12 and the base cover 36 are formed of optically clear material and that the process is accomplished without in any way disturbing the cultured fungi and culture medium.

After the above described microscopic examination of the cultured fungi, permanent slides can be made in accordance with techniques well known in the art. Briefly, with the base cover 36 removed, the cover slip 32 is removed by grasping the lift tab 34 thereof and placing that surface of the cover slip to which the cultured fungi is adhered in contact with a suitable stain carried on a sterile microscope slide (not shown). The lift tab 34 is then removed and the aligned edges of the juxtaposed cover slip 32 and slide (not shown) are sealed with any appropriate sealing substance.

Although the above described usage of the apparatus 10 constitutes the preferred method of culturing and examining fungi, it will be obvious that the method can be modified somewhat without detrimental effects. For example, the method can be accomplished by starting with a base 12 that has been suitably sterilized. In this method, the next step will be filling of the compartment 16 with the culture medium 22 until that medium is flush with the planar surface of the base. From this point on, the method is identical with the previously described method. Thus, it will be seen that the only differences which exist between the two methods is that the first method is employed when the apparatus 10 has been previously prepared and is removed from storage, whereas, the second method relates to preparation and immediate usage of the apparatus and thus includes the steps of sterilization and placing the culture medium 22 into the compartment 16 of the base 12, and does not include the usage of the sealing membrane 24.

While the principles of the invention have now been made clear in an illustrated embodiment, there will be immediately obvious to those skilled in the art, many modifications of structure, arrangements, proportions, the elements, materials, and components used in the practice of the invention, and otherwise, which are particularly adapted for specific environments and operation requirements without departing from those principles. The appended claims are therefore intended to cover and embrace any such modifications within the limits only of the true spirit and scope of the invention.

What I claim is:

1. An apparatus for culturing and examining fungi comprising:
    (a) a base of optically clear material and configured with a planar top surface and a compartment formed therein so as to open upwardly onto the top planar surface thereof, the compartment of said base being formed with square corners and flat surfaces to allow the passage of light rays with minimal refraction;
    (b) a culture nutrient medium in jelled form within the compartment of said base and disposed to present a planar top surface which is flush with the planar top surface of said base;
    (c) membrane means removably affixed on the top planar surface of said base so as to span the compartment thereof in contiguous engagement with the top surface of said culture nutrient medium to preserve the sterile state and moisture content thereof until ready for use;
    (d) a cover slip supported on the top planar surface of said base adjacent the compartment thereof, said cover slip having a surface area which is larger than the open top of the compartment formed in said base and is movable into a position which spans the compartment and is in contiguous engagement with the top surface of said culture nutrient medium subsequent to removal of said membrane means; and
    (e) a base cover of optically clear material demountably positioned on said base.

2. An apparatus as claimed in claim 1 wherein said base cover includes a flat planar top surface to allow the passage of light rays with minimal refraction.

3. An apparatus as claimed in claim 1 wherein said cover slip is provided with a lift tab on one edge thereof.

4. An apparatus as claimed in claim 1 wherein said membrane means comprises a sheet of nonporous material adhesively affixed to the planar top surface of said base.

5. An apparatus as claimed in claim 4 wherein said sheet is transparent and has a lift tab affixed to one edge thereof.

6. An apparatus as claimed in claim 1 wherein said cover includes a flat planar top with an endless sidewall integrally depending therefrom for enclosing said base.

* * * * *